United States Patent
Lacoste et al.

(10) Patent No.: US 10,941,094 B2
(45) Date of Patent: Mar. 9, 2021

(54) METHOD FOR MANUFACTURING CALCIUM DIGLYCEROXIDE

(71) Applicant: EASYL, Bonneville (FR)

(72) Inventors: François Lacoste, Neuilly sur Seine (FR); Valentin Lair, Chaumont (FR); Julien Thiel, Arbusigny (FR); Samy Halloumi, La Roche sur Foron (FR)

(73) Assignee: EASYL, Bonneville (FR)

( * ) Notice: Subject to any disclaimer, the term of this patent is extended or adjusted under 35 U.S.C. 154(b) by 45 days.

(21) Appl. No.: 16/337,445

(22) PCT Filed: Sep. 29, 2017

(86) PCT No.: PCT/FR2017/052675
§ 371 (c)(1),
(2) Date: Mar. 28, 2019

(87) PCT Pub. No.: WO2018/060654
PCT Pub. Date: Apr. 5, 2018

(65) Prior Publication Data
US 2020/0031747 A1    Jan. 30, 2020

(30) Foreign Application Priority Data

Sep. 29, 2016 (FR) ...................... 1659382

(51) Int. Cl.
*C07C 29/70* (2006.01)
*C07C 29/76* (2006.01)
(Continued)

(52) U.S. Cl.
CPC .............. *C07C 29/78* (2013.01); *C07C 29/70* (2013.01); *C07C 29/76* (2013.01); *C07C 31/30* (2013.01)

(58) Field of Classification Search
None
See application file for complete search history.

(56) References Cited

U.S. PATENT DOCUMENTS 8,822,737 B2    9/2014    Houseman et al.
2014/0335229 A1   11/2014   Houseman et al.

FOREIGN PATENT DOCUMENTS

EP    2 323 964 B1    10/2013
JP    2009297669 A  * 12/2009

OTHER PUBLICATIONS

English translation of Patent No. JP2009297669A, Published Dec. 24, 2009, pp. 1-17 (Year: 2009).*
(Continued)

*Primary Examiner* — Medhanit W Bahta
(74) *Attorney, Agent, or Firm* — Nixon & Vanderhye (57) ABSTRACT

A method for manufacturing calcium diglyceroxide crystals includes at least the following steps: placing at least one calcium element source compound, in particular calcium oxide, in suspension in glycerol or in a homogeneous mixture of glycerol and an anhydrous solvent of glycerol, in particular methanol, referred to as the "starting suspension", the molar ratio being greater than or equal to 2; milling the starting suspension at an ambient temperature of less than or equal to 50° C. in a three-dimensional liquid-phase ball mill for a holding time of 15 minutes or less; recovering, at the outlet of the mill, a suspension of calcium diglyceroxide crystals, and optionally, washing the obtained suspension with a glycerol solvent in order to eliminate any excess glycerol, optionally, drying the suspension of calcium diglyceroxide crystals so as to obtain a powder of calcium diglyceroxide crystals. Also disclosed are uses associated with the calcium diglyceroxide crystals.

20 Claims, 8 Drawing Sheets

(51) Int. Cl.
*C07C 31/30* (2006.01)
*C07C 29/78* (2006.01)

(56) References Cited

OTHER PUBLICATIONS

Sanchez-Cantú(Sánchez-Cantú, M. et al. "Direct synthesis of calcium diglyceroxide from hydrated lime and glycerol and its evaluation in the transesterification reaction" Fuel 138 (2014) 126-133) (Year: 2014).*

International Search Report, dated Jan. 19, 2018, from corresponding PCT application No. PCT/FR2017/052675.

Lukic et al., "Calcium diglyceroxide synthesized by mechanochemical treatment, its characterization and application as catalyst for fatty acid methyl esters production", Fuel, 2016, pp. 159-165, vol. 165, XP-002770448.

Li et al., "Transesterification of jatropha oil to biodiesel by using catalyst containing Ca(C2H7O3)2 as a solid base aatalyst", Advanced materials research, 2013, pp. 93-102, vol. 666, ISSN: 1662-8985, XP-002770449.

Sharma et al., "Nanoparticule technology: formulating poorly water-soluble compounds: a review", International Journal of Pharmaceutical Sciences and Research, 2015, pp. 57-71, vol. 6, No. 1, XP-002770498.

* cited by examiner

Figure 3: SEM image of calcium diglyceroxide crystals

Figure 4: Spectrum of calcium diglyceroxide crystals

Figure 5: DTA/TGA curves of calcium diglyceroxide

Figure 6: SEM image of calcium diglyceroxide crystals produced with Zirmill 0.5 mm beads Figure 7: SEM image of calcium diglyceroxide crystals produced with Zirmill 2mm beads Figure 8: SEM image of calcium diglyceroxide crystals produced with Zirmill 2mm beads (sample 241.1)

Figure 9: SEM image of calcium diglyceroxide crystals produced with Ca(OH)$_2$

METHOD FOR MANUFACTURING CALCIUM DIGLYCEROXIDE

TECHNICAL FIELD OF THE INVENTION

The present invention relates to a method for manufacturing calcium diglyceroxide crystals.

In particular, the present invention relates to a method for manufacturing calcium diglyceroxide crystals, performed by micro-milling, particularly without particular heating, a mixture of at least one calcium source compound and glycerol, and optionally an anhydrous solvent of glycerol.

The calcium diglyceroxide crystals obtained with the abovementioned method may be used as a heterogenous catalyst for biodiesel production, and more particularly for the triglyceride transesterification reaction.

TECHNOLOGICAL BACKGROUND

Calcium diglyceroxide, according to the formula $Ca(C_3H_7O_3)_2$ has been the subject of research, particularly with a view to the use thereof as a triglyceride transesterification reaction catalyst.

Lukic et al. in the article "Calcium diglyceroxide synthesized by mechanochemical treatment, its characterization and application as catalyst for fatty acid, methyl esters production", Fuel 165(2016), 159-165 presents in table 1, page 160, the known methods for synthesising calcium diglyceroxide. This article also describes the preparation of said calcium diglyceroxide, from CaO and glycerol according to a molar ratio of 1:5. CaO and glycerol undergo a mechanochemical treatment in a Fritsch planetary ball mill (Pulverisette 5) (2 bottles of 500 cm$^3$ comprising 450 g of 10 mm diameter beads). The milling lasts 5 hours.

Thus, these methods suffer in that they require either a high temperature (greater than 50° C.), or a long reaction time (5 hours) or both.

The publication by Changjun Li et al. "Transesterification of jatropha oil to biodiesel by using catalyst containing $Ca(C_2H_7O_3)_2$ as a solid base catalyst", Advanced materials research, ISSN: 1662-8985, vol. 666, pp 93-102, describes the preparation of calcium diglyceroxide from, on one hand, KOH and glycerol which are heated to 140° C. under constant stirring until KOH dissolution and, on the other, $CaCl_2$) which is dissolved in anhydrous methanol. Both solutions are then mixed (temperature less than 40° C.) so as to carry out a precipitation reaction.

Consequently, this publication describes the manufacture of calcium diglyceroxide by means of a chemical process requiring a plurality of steps (preparation of two solutions) and a high temperature, in this case 140° C.

More general publications relating to nanoparticles are also known from the prior art.

By way of example, the publication by Sharma et al. "Nanoparticle technology: formulating poorly water-soluble compounds: a review", International journal of pharmaceutical sciences and research, 2015; Vol. 6(1):57-71, lists different methods for obtaining nanoparticles. Indeed, it is stated that the therapeutic efficacy of a medicinal product is dependent on the bioavailability thereof and the solubility thereof in water and that these properties may be enhanced as the nanoparticle stage. In the different methods described in this document in order to reduce the size of a starting active ingredient (no chemical reaction), the Dyno Mill wet phase microbead mill is mentioned.

The document EP 2 323 964 is also known from the prior art, describing a method for producing metal glyceroxides from wet glycerol as a biodiesel production by-product and a metal hydroxide, such as calcium hydroxide. The method is carried out under stirring via for example rotary blades (Kenwood kMix food mixer). This method produces an exothermic reaction (temperature ranging from 90 to 140° C.) wherein the calcium hydroxide and water present in the glycerol react.

Consequently, this method involves the drawback of being carried out at high temperatures.

Therefore, the aim of the present invention is that of providing a simple, industrially applicable, method for manufacturing calcium diglyceroxide, particularly not requiring significant heating with an extremely short reaction time.

SUBJECT MATTER OF THE INVENTION

To this end, the present invention provides a method for manufacturing calcium diglyceroxide crystals that comprises at least the following steps:

(1) placing at least one calcium element source compound, in particular calcium oxide (CaO), in suspension in glycerol or in a homogeneous mixture of glycerol ($C_3H_8O_3$) and an anhydrous solvent of glycerol, in particular methanol ($CH_3OH$), referred to as the "starting suspension", the molar ratio of (glycerol):(calcium element source compound(s)) being greater than or equal to 2, preferably from 2 to 10, and in particular from 2 to 5;

(2) milling said starting suspension at an ambient temperature of less than or equal to 50° C., preferably less than or equal to 35° C., in a three-dimensional liquid-phase microbead mill for a holding time of less than or equal to 15 min, preferably less than or equal to 1 minute, and ranging particularly from 5 to 25 seconds and in particular from 10 to 20 seconds;

(3) recovering, at the outlet of the mill, a suspension of calcium diglyceroxide crystals; and (4) optionally, washing the obtained suspension with a glycerol solvent in order to eliminate any excess glycerol;

(5) optionally, said suspension of calcium diglyceroxide crystals is dried so as to obtain a powder of calcium diglyceroxide crystals.

The molar ratio of anhydrous solvent of glycerol (particularly methanol):glycerol may vary from 0 to 30, more particularly from 2 to 15 and preferably from 3 to 12.

Among the anhydrous solvents of glycerol, mention may be made of alkanols, particularly methanol, isopropanol and ethanol. The preferred solvent is methanol.

In particular, the starting suspension comprises no or merely trace levels of water, that is to say at a proportion less than or equal to 3%, preferably less than or equal to 1% and typically less than or equal to 0.3%, by mass, with respect to the total mass of the starting suspension.

According to the invention, "a proportion less than or equal to 3%" comprises the following values: 3; 2; 1; 0.5; 0.4; 0.3; 0.2; 0.1; 0 or any ranges situated between these values.

In the present invention, the term "calcium element source" compound denotes any compound containing calcium element and suitable for supplying during diglyceroxide synthesis the quantity of calcium element required for the formation of calcium diglyceroxide.

Among the calcium element source compounds, mention may be made of CaO or Ca(OH)$_2$, calcium acetate or calcium methanolate, etc. or any of the combinations thereof The preferred calcium source compound is CaO.

The present invention thus makes it possible using at least two starting constituents that are distinct, generally non-nanometric and non-heat-sensitive, to obtain calcium diglyceroxide in a single step.

The present invention also relates to calcium diglyceroxide crystals obtained according to the method described above.

The calcium diglyceroxide crystals obtained according to the method described above may be particularly used for manufacturing a heterogeneous catalyst for biodiesel production.

For the remainder of the description, unless specified otherwise, the indication of a range of values "from X to Y" or "between X and Y", in the present invention, is understood as including the values X and Y.

DETAILED DESCRIPTION OF AN EMBODIMENT EXAMPLE

The invention will be better understood and further aims, features and advantages thereof will emerge more clearly on reading the following description of embodiment examples, with reference to the appended figures wherein.

The applicant endeavoured to develop a novel method for manufacturing calcium diglyceroxide crystals suitable for use on an industrial scale and particularly enabling, by way of example, in the case of the use of CaO as calcium source, the following synthesis:

$CaO + 2C_3H_8O_3 \rightarrow Ca(C_3H_7O_3)_2 + H_2O$.

In particular, the present invention relates to a method for manufacturing calcium diglyceroxide crystals that comprises at least the following steps:

(1) placing at least one mineral compound containing calcium element (CaO, Ca(OH)$_2$, etc.), in suspension in glycerol or in a homogeneous mixture of glycerol (C$_3$H$_8$O$_3$) and an anhydrous solvent of glycerol, for example methanol, referred to as the "starting suspension", the molar ratio of (anhydrous solvent of glycerol):(glycerol) ranging from 0 to 30, more particularly from 2 to 15, and preferably from 3 to 12. The molar ratio of (glycerol):(calcium source compound(s)) being greater than or equal to 2, preferably from 2 to 10, and in particular from 2 to 5;

(2) milling said starting suspension at an ambient temperature of less than or equal to 50° C., preferably less than or equal to 35° C., in a three-dimensional liquid-phase microbead mill for a holding time of less than or equal to 15 min, preferably less than or equal to 1 minute, and ranging particularly from 5 to 25 seconds and in particular from 10 to 20 seconds;

(3) recovering, at the outlet of the mill, a suspension of calcium diglyceroxide crystals; and (4) optionally, washing the obtained suspension with a glycerol solvent (for example methanol) in order to eliminate any excess glycerol.

(5) optionally, said suspension of calcium diglyceroxide crystals is dried so as to obtain a powder of calcium diglyceroxide crystals.

According to the invention, "an ambient temperature less than or equal to 50° C.", comprises the following values: 50; 49; 48; 47; 46; 45; 44; 43; 42; 41; 40; 39; 38; 37; 36; 35; 34; 33; 32; 31; 30; 29; 28; 27; 26; 25; 24; 23; 22; 21; 20; 19; 18; 17; 16; 15; 14; 13; 12; 11; 10; etc. or any ranges situated between these values.

Likewise, according to the invention, "a holding time less than or equal to 15 min" comprises the following values: 15 min; 14 min; 13 min; 12 min; 11 min; 10 min; 9 min; 8 min; 7 min; 6 min; 5 min; 4 min; 3 min; 2 min; 1 min; 55 sec; 50 sec; 45 sec; 40 sec; 35 sec; 30 sec; 25 sec; 20 sec; 15 sec; 10 sec; 5 sec; etc. or any ranges situated between these values.

The applicant thus developed a method that, unexpectedly, is suitable for manufacturing calcium diglyceroxide crystals in a very short time (reaction time less than or equal to 15 minutes and in general, less than or equal to 1 minute), in a single step, at ambient temperature (the method does not require a particular heating step), with a low energy consumption and furthermore an excellent yield.

As will be demonstrated in the tests hereinafter, the method according to the invention further is suitable for obtaining surprisingly calcium diglyceroxide crystals of excellent quality, that is to say of high purity.

The method according to the invention also offers the advantages of having a very reduced cost price (the raw materials used are indeed widely available, non-polluting and inexpensive) and of exhibiting an excellent reproducibility, which distinguishes it further from the methods described in the prior art. The method according to the invention also offers the advantages of being suitable for continuous use. Indeed, these features are important for application on an industrial scale.

Furthermore, despite the extensive research conducted on calcium diglyceroxide crystal synthesis, none has suggested the abovementioned method and in particular a milling step in a three-dimensional microbead mill using a starting suspension comprising calcium oxide (CaO) or another source of calcium and glycerol ($C_3H_8O_3$), optionally in the presence of an anhydrous solvent of gylcerol, such as methanol ($CH_3OH$).

To ensure better understanding of the method according to the invention, a three-dimensional microbead mill suitable for enabling the obtaining of calcium diglyceroxide crystals, and thus within the scope of the invention, will now be described hereinafter with reference to FIGS. 1 and 2.

Figure 1:
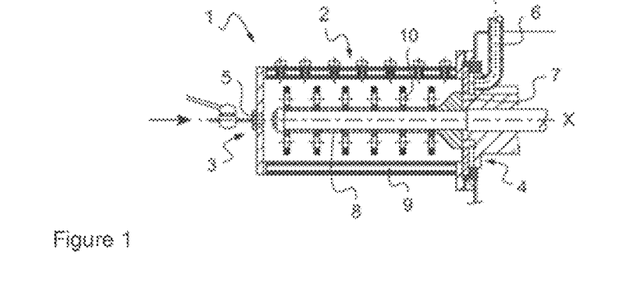
FIG. 1 represents a sectional view along the longitudinal axis XX of a three-dimensional liquid-phase microbead mill, according to an alternative embodiment suitable for the use of the method according to the invention.

As illustrated in FIG. 1, a three-dimensional microbead mill 1 comprises at least:
- a stationary milling chamber 2 of general cylindrical shape extending along a longitudinal axis XX, said chamber 2 being filled at least, in part, with said microbeads (not shown) and comprises: at a first end 3 at least one inlet 5 serving to introduce said starting suspension, and at a second end 4, an outlet 6 including a separating means 7 suitable for only discharging the calcium diglyceroxide suspension formed in said chamber 2; and
- an agitator 8, arranged in the stationary milling chamber 2, presented in the form of an elongated rod along the longitudinal axis XX, said agitator 8 being suitable for setting in motion the microbead/starting suspension assembly.

In particular, the inlet 5 is generally connected to a peristaltic pump (not shown). This pump makes it possible to convey the starting suspension, contained for example in a receptacle, such as a tank, inside the milling chamber 2 via the inlet 5. The pump makes it possible furthermore, during the operation of the three-dimensional mill, to convey this starting suspension according to a certain rate that is adjustable, hereinafter referred to as "flow rate". This flow rate further forms a flow in the milling chamber 2 suitable for carrying the starting suspension from the inlet 5 to the outlet 6.

The outlet 6 of the milling chamber 2 comprises in particular the system 7 for separating the microbeads from the final suspension comprising mostly the calcium diglyceroxide crystals, methanol and optionally the remaining unreacted raw materials. This separation means 7 may be a sieve wherein the orifices exhibit a size less than that of the microbeads or a separating slot wherein the width is also suitable for retaining the microbeads inside the chamber 2.

The internal wall 9 of the milling chamber 2 comprises according to a first embodiment a smooth internal surface. However, according to an alternative embodiment described hereinafter, fingers 11 may be provided on this internal surface 9.

As mentioned above, inside the milling chamber 2 is arranged the agitator 8 which, in addition to the flow rate, also enables the setting in motion of the starting suspension.

In particular, the agitator 8 is suitable for rotating about the axis X via a rotary shaft (14, FIG. 2) to impart inside the milling chamber 2 a swirling motion to the starting suspension and thus carry out intense mixing between this starting suspension and the microbeads present in the chamber 2 along the internal wall 9 of this chamber 2.

In particular, the mill via the rotary shaft 14 has a rotational speed greater than or equal to 100 revolutions per minute, advantageously of 1000 revolutions per minute, preferably greater than or equal to 2000 revolutions per minute and typically greater than or equal to 2500 revolutions per minute.

According to the invention, "a rotational speed greater than or equal to 100 revolutions per minute" comprises the following values: 100; 150; 200; 250; 300; 350; 400; 450; 500; 550; 600; 650; 700; 750; 800; 850; 900; 950; 1000; 1100; 1200; 1300; 1400; 1500; 1600; 1700; 1800; 1900; 2000; 2100; 2200; 2300; 2400; 2500; 2600; 2700; 2800; 2900; 3000; 3100; 3200; 3300; 3400; 3500; 3600; 3700; 3800; 3900; 4000; 4500; 5000; 5500; 6000; etc., or any ranges included between these values.

In general, the mill has a rotational speed ranging from 1000 rpm to 5000 rpm, in particular from 1500 rpm to 4500 rpm, preferably from 2000 rpm to 4000 rpm and typically from 2800 to 3200 rpm.

Figure 2:
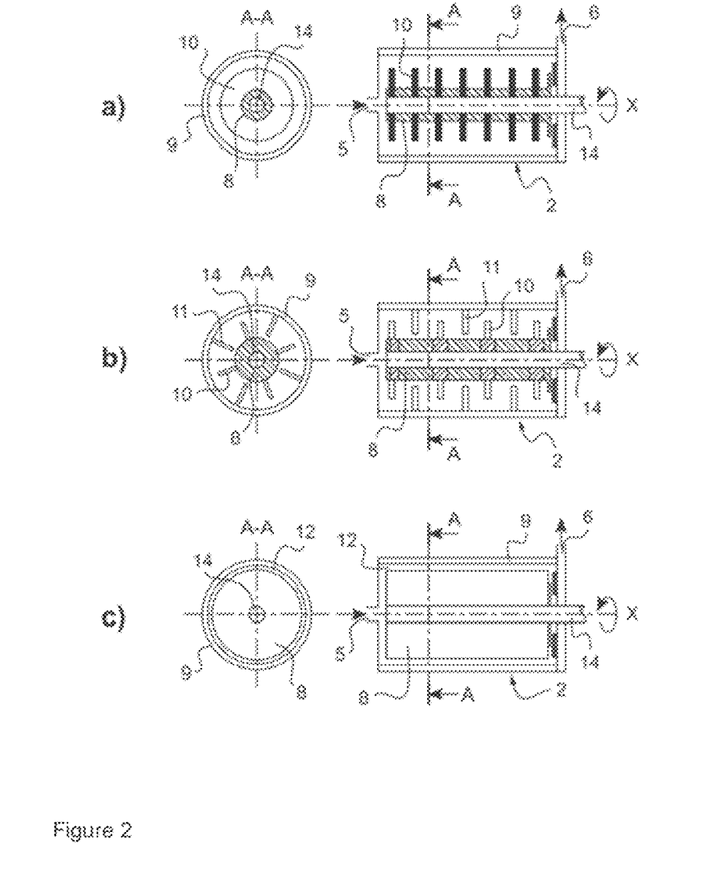
FIG. 2 represents sectional views along the axis XX and the axis AA, of alternative embodiments of three-dimensional liquid-phase microbead mills according to FIG. 1 wherein: (a) the agitator has discs, (b) the agitator includes fingers and (c) the milling chamber is annular.

In order to improve this mixing, the agitator 8, like the internal wall 9 of the chamber 2, may have various possible configurations represented for example in FIG. 2.

According to a first configuration illustrated in FIG. 2a, the agitator 8 comprises along the elongated rod thereof discs 10, arranged perpendicularly thereto. The number thereof may vary from 2 to 8, preferably from 2 to 5. These discs 10 make it possible on one hand, to improve the milling of the starting suspension by mixing the microbeads further and, on the other, to accelerate the reaction time.

According to a second configuration illustrated in FIG. 2b, the agitator 8 may also comprise along the rod thereof one or a plurality of discs 10 arranged perpendicular and that are further suitable for engaging with fingers 11, arranged perpendicularly, with respect to the internal wall 9 of the chamber 2. A finger is presented particularly in the form of a ring which extends perpendicularly from the wall 9. For this configuration, the discs 10 and the fingers 11 are arranged in staggered rows, that is to say the discs 10 and the fingers 11 are arranged in alternation in the chamber 2. Furthermore, the thickness of the rod 8 is increased with respect to the previous configuration (FIG. 2a) such that the periphery of the discs 10 is near the internal wall 9 and that of the fingers 11 is close to the periphery of the rod of the agitator 8. Thus, in this configuration, the volume of the chamber is reduced with respect to the preceding configuration, consequently enabling, superior mixing between the starting suspension, the microbeads and the internal wall 9 of the chamber 2.

The volume of the chamber 2 may further be reduced as illustrated in FIG. 2c. In this configuration, the agitator 8 has an external diameter slightly less than the internal diameter of the chamber 2, thus forming an annular chamber 12 of small volume arranged between the external wall of the agitator 8 and the internal wall 9 of the chamber 2. The microbeads (not shown) are arranged in this annular chamber 12. During the operation of this configuration, the starting suspension is introduced via the inlet 5 with a certain flow rate, that will then pass through the annular chamber 12 to the outlet 6 while being mixed by the microbeads.

In general, the mill suitable for carrying out the method according to the invention comprises a milling chamber having a diameter of 75 mm to 300 mm for a length of 80 mm to 900 mm and an agitator having a size ranging from 65 mm to 260 mm. Thus, the volume of the milling chamber varies from 0.35 L to 600 L, preferably from 0.35 L to 400 L, and typically from 0.35 L to 62 L.

According to the invention, "a milling chamber volume ranging from 0.35 L to 600 L" comprises the following values: 0.35; 0.5; 0.8; 1; 2; 3; 4; 5; 6; 7; 8; 9; 10; 15; 20; 25; 30; 35; 40; 45; 50; 55; 60; 65; 70; 80; 85; 90; 100; 110; 120; 130; 140; 150; 160; 170; 180; 190; 200; 210; 220; 230; 240; 250; 260; 270; 280; 290; 300; 350; 400; 450; 500; 550; 600 etc., or any ranges included between these values.

The geometry of the milling chamber and the agitator may be adjusted by a person skilled in the art according to the quantity of calcium diglyceroxide crystals sought, as well as the reaction time sought. For example, it is also possible that the milling chamber 2 comprises an accelerator in order to improve the milling of the starting suspension.

Furthermore, the microbeads housed in the milling chamber 2 and suitable for the method according to the invention are substantially of spherical shape and have a mean diameter less than or equal to 5 mm, generally ranging from 0.05 mm to 4 mm, preferably from 0.2 to 3 mm, in particular from 0.3 to 2 mm, and typically of the order of 0.5 to 1 mm. Preferably, the diameter of the microbeads is less than or equal to 1 mm and is typically of the order of 0.05 mm to 1 mm.

They are preferentially chosen among the microbeads having a high hardness and a relatively good abrasion resistance.

In particular, the microbeads have a Vickers hardness measured as per the EN ISO 6507-1 standard greater than or equal to 900 HV1, preferably ranging from 900 HV1 to 1600 HV1, typically ranging from 1000 to 1400 HV1 and particularly ranging from 110 to 1300 HV1.

According to the invention, "a Vickers hardness greater than or equal to 900 HV1" comprises the following values: 900; 910; 920; 930; 940; 950; 960; 970; 980; 990; 1000; 1010; 1020; 1030; 1040; 1050; 1060; 1070; 1080; 1090; 1000; 1110; 1120; 1130; 1140; 1150; 1160; 1170; 1180; 1190; 1200; 1300; 1400; 1500; 1600; 1700; etc., or any ranges included between these values.

Advantageously, they have a high true density. In general, the microbeads according to the invention have a true density greater than or equal to 2 g/cm$^3$, in particular ranging from 2 to 15 g/cm$^3$, preferably from 3 to 12 g/cm$^3$, and typically from 4 to 10 g/cm$^3$.

Thus, the microbeads according to the invention may be ceramic microbeads, (zirconium oxide $ZrO_2$, zirconium silicate $ZrSiO_4$); steel microbeads, tungsten carbide microbeads, glass microbeads or any of the combinations thereof.

Preferably, the microbeads are made of ceramics as they do not generate pollution due to the wear thereof.

In particular, the microbeads are made of zirconium oxide.

Optionally, the zirconium oxide microbeads may be stabilised by another oxide, such as cerium oxide, yttrium oxide and/or silicon.

By way of examples, the following compositions, summarised in table 1 hereinafter, are suitable for forming the microbeads according to the invention:

TABLE 1

| Microbead composition | Hardness HV1 | True density (g/cm$^3$) | Manufacturer |
|---|---|---|---|
| Zirconium oxide microbeads stabilised with cerium oxide 80% $ZrO_2$ 20% CeO | 1180 | ≥6.10 | Saint-Gobain (Zirmil ®Y Ceramic Beads) or EIP (Procerox ® ZO Cer) |
| Zirconium oxide microbeads stabilised with yttrium 95% $ZrO_2$ <5% $Al_2O_3$ Remainder: $Y_2O_3$ | 1250 | ≥5.95 | EIP (Procerox ® ZO (Y)) |
| Zirconium oxide microbeads stabilised with yttrium and silicon: 78% $ZrO_2$, 12% $SiO_2$, 5% $Al_2O_3$ et 4% $Y_2O_3$ | >700 | >4.80 | Saint-Gobain (ER120 Ceramic Beads) |

TABLE 1-continued

| Microbead composition | Hardness HV1 | True density (g/cm$^3$) | Manufacturer |
|---|---|---|---|
| Zirconium silicate $ZrSiO_4$ microbeads | ≥800 | >6.5 | Saint-Gobain (Rimax Ceramic Beads) |
| Glass microbeads | 500 | >3.76 | — |
| Steel microbeads | 700 | >7.7 | — |

Generally, the microbeads suitable for the method according to the invention are not made of glass or exclusively of glass.

In particular, the microbeads represent, in volume, with respect to the total volume of the stationary chamber 2 from 50% to 85%, preferably from 55% to 70%.

According to the invention, "a volume from 50 to 85%" comprises the following values: 50; 55; 60; 65; 70; 75; 80; 85; etc., or any ranges included between these values.

By way of example, the three-dimensional liquid-phase microbead mill suitable for carrying out the method according to the invention may correspond to mills marketed by the companies WAB, Dyno-Mill range: Multi Lab, ECM and KD, NETZCH or Alpine Hosokawa, for example, Agitated Media Mill AHM.

The manufacturing method according to the invention will now be described more explicitly hereinafter.

As mentioned above, the manufacture of the calcium diglyceroxide crystals according to the invention comprises firstly (1) placing a Ca element source compound, for example calcium oxide (CaO), or a mineral compound containing calcium element (Ca(OH)$_2$, etc.) in suspension in glycerol ($C_3H_8O_3$), optionally in a homogeneous mixture with an anhydrous solvent of glycerol such as methanol ($CH_3OH$), referred to as the "starting suspension".

The starting suspension is conventionally prepared by mixing the raw material (CaO+$C_3H_8O_3$) optionally with the anhydrous solvent (methanol) in a suitable apparatus, such as a receptacle or a tank, equipped with a stirring system (such as a magnetic stirrer, stirring blades, etc.). The apparatus and the stirring system may be adapted by a person skilled in the art according to the quantity of calcium diglyceroxide crystals to be manufactured.

Preferably, the calcium element source compound and glycerol are mixed in stoichiometric proportions.

In particular, calcium oxide and glycerol are mixed, preferably, in stoichiometric proportions in the starting suspension to produce the reaction:

$CaO+2C_3H_8O_3 \rightarrow Ca(C_3H_7O_3)_2+H_2O$

This is equivalent, in mass proportions to 56 kg of CaO for 184 kg of glycerol, or 23.3% CaO and 76.6% glycerol. Thus, the starting suspension is generally free from water or the latter is only present at trace levels in the suspension.

It is obviously possible to deviate substantially from the stoichiometric proportion, for example, by mixing from 18 to 28%, by mass of CaO, with respectively from 72 to 82% by mass of glycerol, with respect to the total weight of CaO+glycerol, if for example a calcium diglyceroxide composition containing an excess either of glycerol, or of calcium oxide, is sought.

The presence of methanol, not required for the reaction (optional), promotes the setting in motion of the microbeads of the mill for superior milling of the starting suspension and therefore superior calcium diglyceroxide crystal synthesis.

In general, the calcium element source compound of the starting suspension is found in powder form. This powder has a particle size less than or equal to 100 µm, preferably less than or equal to 50 µm, in particular less than or equal to 30 µm, such as 20 µm or 10 µm. Thus, it is not necessary for the calcium source element to be on the nanometric scale.

The calcium oxide suitable for the present invention has preferably a particle size less than or equal to 200 µm and preferably less than or equal to 100 µm, and in particular the particle size ranges from 0.01 µm to 20 µm. The calcium oxide having the CAS number: 1305-78-8 and marketed for example by Sigma Aldrich of purity greater than or equal to 99% is suitable for carrying out the method according to the invention.

The glycerol suitable for the present invention is found in liquid form. The glycerol having the CAS number: 56-81-5 and marketed for example by Mon-droguiste.com of purity greater than or equal to 99.5% is suitable for carrying out the method according to the invention.

Preferably, the calcium oxide and the glycerol have a high purity, generally greater than or equal to 90%, in particular greater than or equal to 95% and typically greater than or equal to 99%, or even greater than or equal to 99.9%.

Once the starting suspension has been prepared, it is conveyed to the three-dimensional microbead mill 1 generally by means of the adjustable flow rate peristaltic pump via the inlet 5. The peristaltic pump makes it possible to continue mixing the starting suspension prior to entering the chamber 2. Furthermore, as mentioned above, this pump makes it possible to introduce the starting suspension into the chamber 2 with a controlled flow rate.

Generally, the starting suspension is introduced at a flow rate greater than or equal to 10 L/h.

According to the invention, "a flow rate greater than or equal to 10 L/h" comprises the following values: 10 L/h; 15 L/h; 20 L/h; 25 L/h; 30 L/h; 35 L/h; 40 L/h; 45 L/h; 55 L/h; 60 L/h; 65 L/h; 70 L/h; 80 L/h; 85 L/h; 90 L/h; 95 L/h; 100 L/h; 110 L/h; 120 L/h; 130 L/h; 140 L/h; 150 L/h; 50 L/h; 55 L/h; 60 L/h; 65 L/h; 70 L/h; 75 L/h; 80 L/h; 85 L/h; 90 L/h; 95 L/h; 100 L/h; 105 L/h; 110 L/h; 115 L/h; 120 L/h; 125 L/h; 130 L/h; 135 L/h; 140 L/h; 145 L/h; 150 L/h; 155 L/h; 160 L/h; 165 L/h; 170 L/h; 175 L/h; 180 L/h; 200 L/h; 300 L/h; 400 L/h; 500 L/h; 600 L/h; 700 L/h; 800 L/h; 900 L/h; 1 m$^3$/h; 2 m$^3$/h; 3 m$^3$/h; 4 m$^3$/h; 5 m$^3$/h; 6 m$^3$/h; 7 m$^3$/h; 8 m$^3$/h; 9 m$^3$/h; 10 m$^3$/h; 11 m$^3$/h; 12 m$^3$/h; 13 m$^3$/h; 14 m$^3$/h; 15 m$^3$/h; etc., or any ranges included between these values.

In particular, the starting suspension is introduced at a flow rate ranging from 10 to 130 L/h, preferably ranging from 20 to 100 L/h and typically ranging from 30 to 90 L/h.

Obviously, the flow rates may vary according to the size of the three-dimensional microbead mill used to carry out the method. For example, for a three-dimensional microbead mill having a stationary chamber 2 of 0.5 L of volume, the flow rate may be of the order of 40 to 150 L/h, such as about 45 L/h; whereas for larger-sized mills having in particular a stationary chamber 2 of 60 L, the flow rate may be of the order of 2 to 15 m$^3$/h, such as about 4 m$^3$/h.

Once the starting suspension has been introduced into the chamber 2, the milling step (2) commences.

Under the effect of the flow created by the flow rate, the starting suspension passes through the stationary chamber 2 from the inlet 5 to the outlet 6, while being set in motion by the agitator 8 which enables intense mixing of this suspension with the microbeads and, if applicable, with the discs 10, fingers 11, etc., along the internal wall 9 of the chamber 2.

The rotational speed of the agitator may for example vary from 4 to 20 Pi rad/s, preferably from 4 to 8 Pi rad/s.

The holding time of the starting suspension is less than or equal to 15 min, preferably less than or equal to 5 minutes, in particular less than or equal to 1 minute, and ranges particularly in the mill from 5 to 25 seconds and in particular from 5 to 20 seconds, such as from 1 to 15 seconds. It is indeed inherent to the bulk volume of the beads and to the flow rate.

For example, if the total bulk volume of the beads is 270 cm$^3$ (beads of bulk density of 3.7 g/cm$^3$) and the suspension feed rate is 45 L/h, or 12.45 cm$^3$/s, then the holding time of the suspension in the chamber 2 is estimated at about 22 seconds. Consequently, the holding time may be advantageously adjusted, for example by controlling the bulk density of the microbeads, as well as the flow rate.

The term "bulk volume" denotes the volume of the microbeads including the interstitial air between the beads. The bulk density is the ratio between the mass of the microbeads and the bulk volume.

Furthermore, by adjusting the size of the microbeads and the flow rate, more or less fine crystals may be obtained. For example, finer milling may be obtained if the flow rate of the starting suspension is slowed down.

The milling step may be carried out in continuous mode or discontinuous mode in one or a plurality of passages (pendular or recirculating mode).

When carried out in discontinuous mode, the number of passages of the so-called starting suspension may be from 1 to 10, preferentially from 1 to 5 (that is to say, after a first passage, the suspension is recovered at the outlet 6 and reinjected once again, by means of the pump, into the chamber 2 via the inlet 5 to enable a second passage). In particular, the number of passages of the starting suspension is 1.

Indeed, the applicant observed that a single passage in the microbead mill, despite a very short holding time, made it possible to obtain at the outlet 6 a suspension comprising very predominantly calcium diglyceroxide crystals (particularly when the starting materials are in stoichiometric proportions), of very satisfactory purity and size.

Thus, this milling step will be carried out preferably in continuous mode.

Advantageously, this milling step is carried out at an ambient temperature less than or equal to 50° C., that is to say most frequently at an ambient temperature ranging from 15° C. to 45° C., in particular from 18° C. to 35° C. and in general is of the order of 20° C. to 25° C. Indeed, the method according to the invention requires no particular heating in order to manufacture the calcium diglyceroxide crystals, contrary to the teaching disclosed in the prior art. Thus, the starting reagents/starting suspension are/is introduced into the mill at ambient temperature (generally around 20-25° C.). However, depending on the starting reagents used, an exothermic reaction may take place during this milling step and the temperature may rise slightly (generally the temperature at the mill outlet is less than or equal to 50° C.).

Once the milling step has been carried out, (3) the calcium diglyceroxide suspension is recovered at the outlet 7 of the mill 1 and is optionally (4) washed of the traces of excess glycerol using methanol, and optionally (5) dried so as to obtain a calcium diglyceroxide powder.

According to an alternative embodiment, the calcium diglyceroxide suspension may be air-dried. Indeed, it has emerged that the carbonation reaction is very slow between calcium diglyceroxide and the $CO_2$ in the air.

According to a further alternative embodiment, the calcium diglyceroxide suspension may be dried at a temperature of 50 to 100° C. for 1 to 4 hours.

The final product is generally stored until the use thereof in the form of paste or mixed with a solvent. It may also be recovered in solid form and stored in a tight receptacle.

As demonstrated in the tests hereinafter, homogeneous calcium diglyceroxide crystals are obtained, of overall parallelepiped shape.

The calcium diglyceroxide crystals obtained using the method according to the invention generally has the following population distributions according to the grain size distribution measured with a liquid process laser granulometer:

0.5 µm≤$D_x50$≤50 µm, preferably 1 µm≤$D_x50$≤0.10 µm and

1 µm≤$D_x90$≤75 µm, preferably 5 µm≤$D_x90$≤40 µm.

Furthermore, as mentioned above, the characteristics of the calcium diglyceroxide crystals (size, thickness, etc.) may be adjusted, according to the needs of the envisaged use, by varying some parameters, such as the flow rate, the microbead diameter of the anhydrous solvent of glycerol content in the starting suspension.

The present invention may relate to the use of the calcium diglyceroxide crystals obtained according to the abovementioned method.

The calcium diglyceroxide may be used a heterogeneous catalyst for biodiesel production as mentioned in the publication "Direct synthesis of calcium glyceroxide from hydrated lime and glycerol and its evaluation in the transesterification reaction" published in the journal "Fuel 138 (2014)-126 to 133".

In particular, the calcium diglyceroxide may be used as a heterogeneous catalyst for biodiesel production by reacting methanol with plant oils.

Further applications of catalysis may be envisaged, particularly those requiring a base catalyst such as Bronsted.

EXAMPLES

The description of the tests hereinafter is given merely by way of illustrative and non-limiting example.

A° Characterisation

SEM

Scanning electron microscopy (SEM) was carried out on a Zeiss EVO MA 15 apparatus, with secondary and backscattered electrons (chemical contrast) with a primary beam of 5 to 20 kV.

To carry out the SEM tests, the calcium diglyceroxide crystal suspensions were previously air-dried at 50° C. so as to obtain a powder.

XRD

The X-ray diffractometry (XRD) spectra were collected with a D8 ADVANCE Series II diffractometer marketed by Bruker using CuKα1 radiation (0.15406 nm) according to the Bragg-Brentano configuration.

The detector used is a LynxEye 1D detector from Bruker. The aperture of the detector is 3° (150 bands).

The XRD measurements were made between 10° and 120° (at the scale 2θ) with a step of 0.008° (1 s/step).

To carry out the XRD tests, the calcium diglyceroxide crystal suspensions were likewise previously air-dried at 50° C., so as to obtain a powder. Four consecutive scans were carried out in order to confirm the progression over time of the powder studied.

Liquid-Process Granulometry

The liquid-process granulometry measurements were made with a Mastersizer 3000E model laser granulometer from Malvern.

For this measurement, 5 cm³ of the calcium diglyceroxide crystal suspension samples were previously dispersed in a receptacle having a diameter of 40 mm using a 28 khz/40 khz ultrasound generator equipped with a 20 mm diameter sonotrode.

This measurement gives the distribution in volume (as %) of the particles of the sample for each grain size class in µm (which is equivalent to the longest calcium diglyceroxide crystal length).

DTA/TGA

The differential thermal (DTA) and thermogravimetric (TGA) analyses were carried out with a Linseis STA PT1000 model combined DTA/TGA apparatus.

The analyses were performed in air, with a temperature gradient of 10° C./min, ranging from 20° C. to 900° C.

To carry out the tests, the calcium diglyceroxide crystal suspensions were previously air-dried at 50° C., so as to obtain a powder.

B° Test Sample Preparation Procedure

Apparatus

The tests were performed in a Dyno Mill MultiLab three-dimensional microbead mill from Willy A. Bachofen AG containing 1 kg of microbeads.

The microbeads are made of zirconium oxide and have a diameter of 0.5, 1.0 or 2.0 mm. The characteristics of the microbeads used for the tests are summarised in table 2 hereinafter:

TABLE 2

| Beads | 500 µm | 1.0 mm | 2.00 mm |
|---|---|---|---|
| Composition (% by mass) | 93% $ZrO_2$ 5% $Y_2O_3$ 2% others | 93% $ZrO_2$ 5% $Y_2O_3$ 2% others | 93% $ZrO_2$ 5% $Y_2O_3$ 2% others |
| Specific density | 6 g/cm³ | 6 g/cm³ | 6 g/cm³ |
| Bulk density | 3.7 kg/L | 3.7 kg/L | 3.7 kg/L |
| Vickers hardness | 1250 HV1 | 1250 HV1 | 1250 HV1 |

The 500 µm microbeads are particularly marketed under the trade name Zirmil® Y Ceramic Beads by Saint-Gobain.

The milling chamber of the mill has a capacity of 309 mL and is filled, in volume, with respect to the total volume thereof and according to the tests, to 80% with the microbeads described above.

In operation, the microbeads are placed under stirring by an agitator at a rotational speed of 2890 rpm. The agitator further includes two 64 mm diameter polyurethane mixing discs.

Raw Materials

For the tests, the starting raw materials are: calcium oxide (CaO) having a purity≥99% marketed by Sigma Aldrich, and glycerol of purity≥99.5% marketed by Mon-droguiste.com.

General Operating Procedure for Tests:

To carry out each test hereinafter, the following steps are carried out:

a starting suspension is prepared in a beaker using calcium oxide and glycerol, in stoichiometric proportions, in an anhydrous solvent of glycerol (methanol), then the starting suspension is placed under stirring using a magnetic stirrer;

it is then conveyed, via an adjustable flow rate peristaltic pump to the Dyno Mill MultiLab mill described above: the flow rate in the mill may be up to 60 L/h. In this test, it was set to 45 L/h corresponding to a holding time of 8 s;

the starting suspension is then milled in the mill containing microbeads 0.5 mm; 1 mm or 2 mm in diameter for a given time (which is dependent on the flow rate of the starting suspension) at ambient temperature (20-25° C.), thus make it possible, at the mill outlet, to obtain a calcium diglyceroxide crystal suspension;

finally, the calcium diglyceroxide crystal suspension is recovered.

Figure 3:
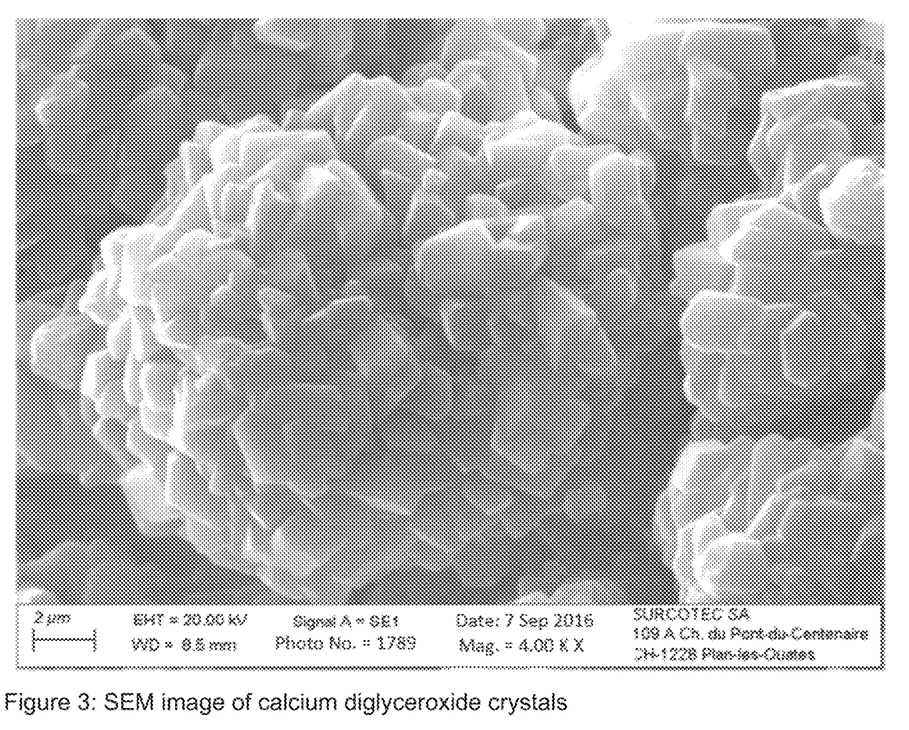
FIG. 3 is a scanning electron microscopy (SEM) photo of calcium diglyceroxide crystals obtained according to the method according to the invention using the following parameters: starting suspension comprising 980 g of raw materials (glycerol+CaO) with a molar ratio of (glycerol):(CaO) equal to 5, in 1 kg of anhydrous solvent of glycerol (herein, methanol); a flow rate of the starting suspension in the mill of 45 L/h and a bead diameter of 500 µm.
Figure 4:
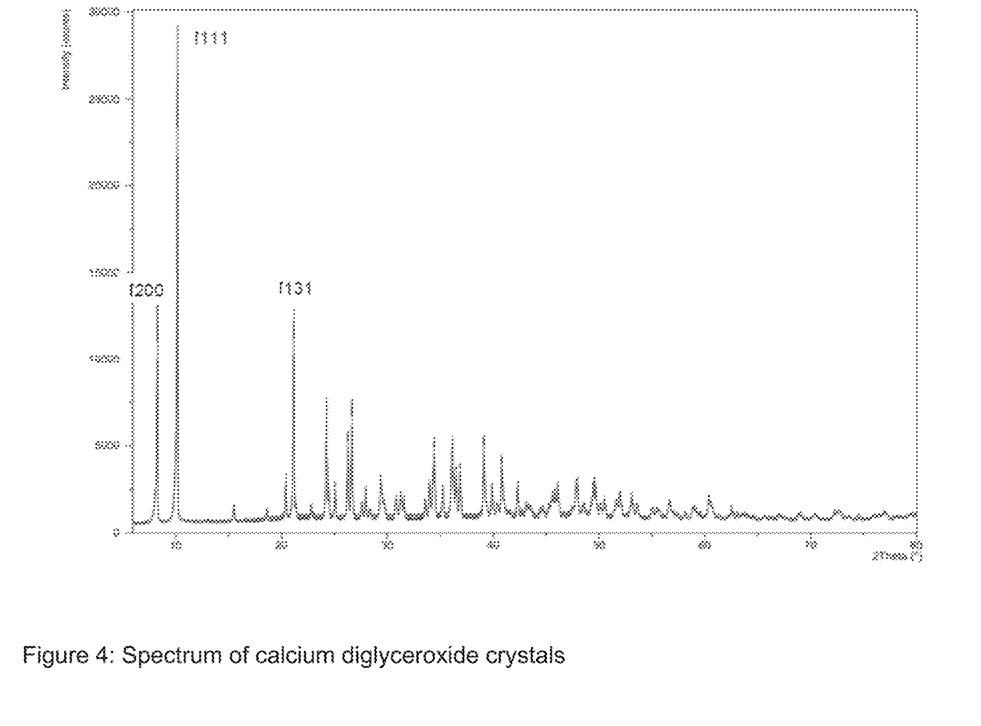
FIG. 4 is an X-ray diffractometry (XRD) spectrum of calcium diglyceroxide crystals obtained under the same experimental conditions as those in FIG. 3.
Figure 5:
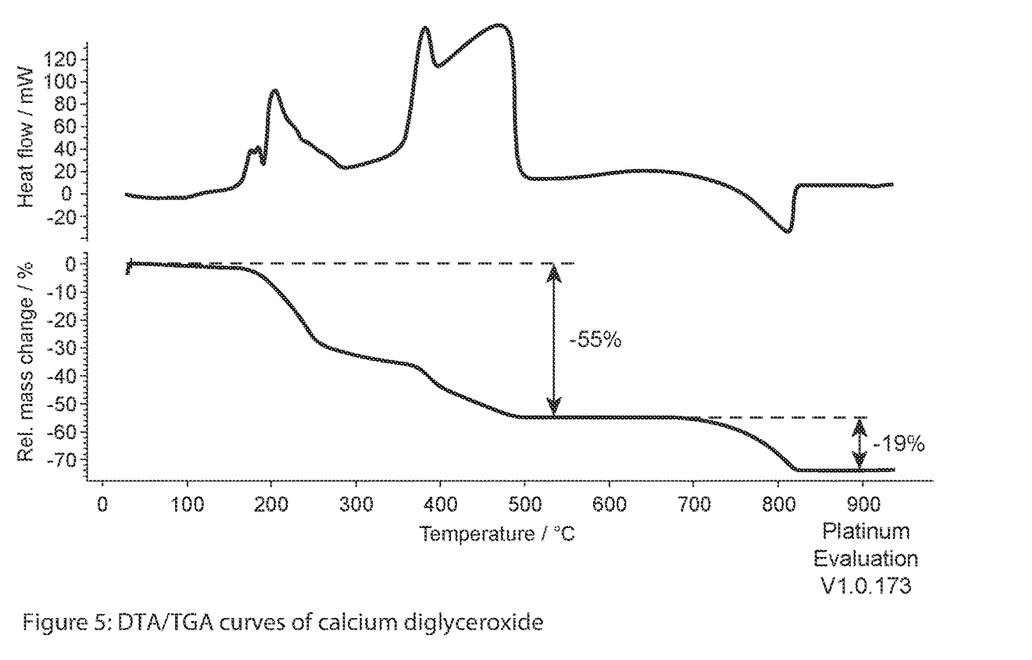
FIG. 5 are DTA/TGA curves of the calcium diglyceroxide obtained.

C° Characterisation of the Calcium Diglyceroxide Crystals Obtained (FIGS. 3, 4 and 5)

As can be seen in FIG. 3, according to the method according to the invention, after merely one passage in the microbead mill and thus a holding time of 8 seconds, the calcium diglyceroxide crystals are obtained (instead of much longer times, of up to several hours, according to the methods according to the prior art).

The following parameters were used: starting suspension comprising 980 g of raw materials (glycerol+CaO with a molar ratio of (glycerol):CaO equal to 5, in 1 kg of anhydrous solvent of glycerol (herein, methanol); a flow rate of the starting suspension in the mill of 45 L/h and a bead diameter of 500 µm;

With reference to FIG. 4, it is observed that the lines of the four XRD spectra, scanned successively, are fully conforming with respect to those of the reference spectrum of calcium diglyceroxide, known to those skilled in the art (CDDC deposition ref #828033), both for the angular positions thereof and for the relative intensities thereof, that is to say:

The presence of the three primary peaks is observed (crystallographic planes [200], [111] and [131]), at respectively 8.281°/10.177° and 21.179°, All the other significant peaks are present at the envisaged angles, such as 20.436°/24.466°/25.071°/26.671°/27.973°/34.446°/36.505°/36.894°/39.130°/40.850;

with substantially the envisaged intensities,

These XRD spectra also demonstrate that the sample analysed has an excellent purity. Indeed, no contamination is recorded:

the primary peaks of CaO (as per JCPDS 037-1481), which are at 30.204°/37.347° and 53.856° do not appear therein;

the primary peaks of Ca(OH)2 (as per JCPDS 044-1481), which are at 18.008°/28.672°/34.102° likewise do not appear therein;

and the primary peak of CaCO3 (as per JCPDS 005-0586) which is at 29.4° is not significantly present.

Finally, the TGA/DTA spectra presented in FIG. 5 are conforming with respect to the behaviour of calcium diglyceroxide crystals. This behaviour was particularly described by L. Leon-Reina et al. in the publication entitled "Structural and surface study of calcium glyceroxide, an active phase for biodiesel production under heterogeneous catalysis" dated 2013 and published in the Journal of Catalysis 300. The two characteristic outcomes are thus observed:

A loss of mass of about 55% between 180° C. and 500° C., which may correspond to the breakdown of calcium diglyceroxide to calcium carbonate, which would induce a theoretical loss of mass of 55%.

A loss of mass of about 19% between 700° C. and 850° C., which may correspond to the decarbonation of calcium carbonate to calcium oxide, which would be marked by a theoretical loss of mass of 19.8%.

In conclusion, the method according to the invention makes it possible to immediately obtain very pure calcium diglyceroxide crystals.

D° Influence of Bead Diameter and Type

The purpose of this example is to determine whether the size and composition of the beads used when carrying out the method have an influence on the quality of the calcium diglyceroxide crystals obtained.

Figure 6:
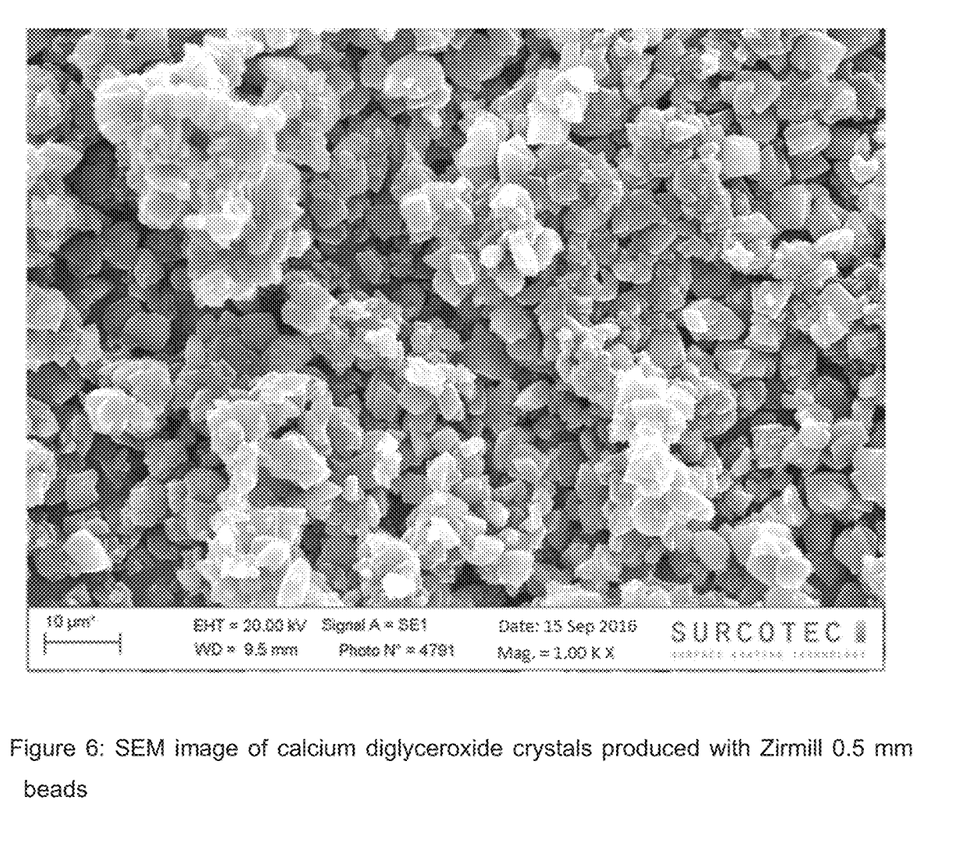
FIGS. 6, 7 and 8 are SEM microphotographs of the calcium diglyceroxide crystals obtained using 0.5 mm and 2 mm zirconia beads and 2 mm silica beads, respectively.
Figure 7:
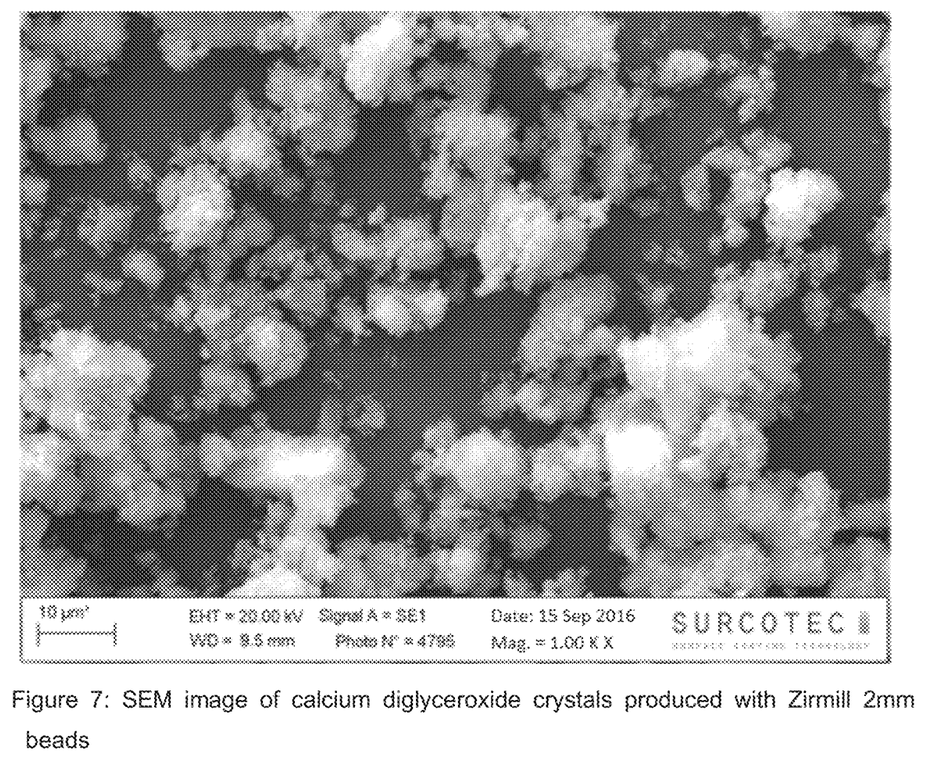
Figure 8:
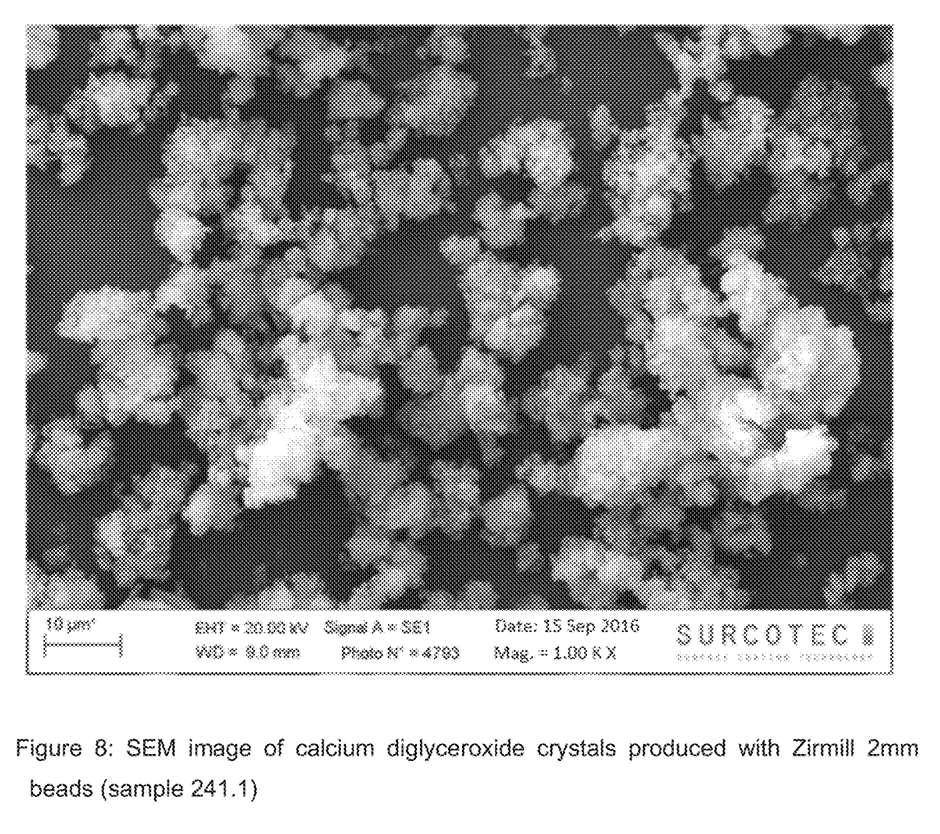

Similarly to the tests in the previous example, the calcium diglyceroxide crystals were synthesised according to the general procedure mentioned above and using in particular the following parameters:

A starting suspension containing 980 g of raw materials (CaO+glycerol) with a molar ratio of (glycerol):(CaO) equal to 5, per 1 kg of anhydrous solvent of glycerol (methanol);

A flow rate of 45 L/h;

Milling beads of 500 µm or 2 mm in diameter, that may be predominantly made up of $SiO_2$ (Silibeads® type S) or predominantly made up of $ZrO_2$ (Zirmil® Y Ceramic Beads);

And only carrying out a single passage in the mill;

The results of these tests are illustrated in FIGS. 6 to 8.

According to the SEM images, it is observed that the conversion of calcium oxide and glycerol into calcium diglyceroxide is very close to 100%, regardless of the size or composition of the beads used.

Likewise, it was observed that, regardless of the type of beads or the diameter thereof, the size of the calcium diglyceroxide crystals is substantially constant. In particular, the following grain size distribution is obtained (table 3):

TABLE 3

| Tests | Dx(10) (µm) | Dx(50) (µm) | Dx(90) (µm) |
| --- | --- | --- | --- |
| 1) $ZrO_2$ beads 500 µm | 0.96 | 2.4 | 8.69 |
| 2) $SiO_2$ beads 500 µm | 1.08 | 2.85 | 9.10 |
| 3) $ZrO_2$ beads 2 mm | 1.12 | 3.13 | 8.69 |
| Mean | 1.05 | 2.79 | 8.83 |
| Standard deviation | 0.08 | 0.37 | 0.24 |

Thus, the method, according to the invention, makes it possible to obtain homogeneous calcium diglyceroxide crystals of small sizes (Dx(50)) preferably between 1 and 10 µm and particularly between 1 and 5 µm).

E/ Grain Size Distribution of Calcium Diglyceroxide Crystals According to Number of Passages For this example, different numbers of passages in the three-dimensional mill were tested (1 and 45 passages), in order to check the impact thereof on the grain size distribution of the calcium diglyceroxide crystals obtained.

Thus, the calcium diglyceroxide crystals tested were synthesised according to the general procedure mentioned above and using the following parameters:

A starting suspension containing 306 g of raw materials (CaO+glycerol) with a molar ratio of (glycerol):(CaO) equal to 2, per 1 kg of anhydrous solvent of glycerol (methanol);

A flow rate of 45 L/h;

500 μm milling beads predominantly made up of $ZrO_2$ (Zirmil® Y Ceramic Beads);

And carrying out a single or 45 passages in the mill;

The grain size distribution is as follows (Table 4):

TABLE 4

| Tests | Dx(10) (μm) | Dx(50) (μm) | Dx(90) (μm) |
|---|---|---|---|
| 1 passage | 1.08 | 3.23 | 9.99 |
| 45 passages | 0.41 | 0.82 | 6.43 |

It is observed that a greater number of passages makes it possible to obtain smaller sized crystals.

Thus, the method according to the invention makes it possible to obtain calcium diglyceroxide crystals, the size whereof may be adapted readily by modifying the number of passages in the mill.

F° Characterisation of the Calcium Diglyceroxide Crystals Obtained Using Another Calcium Source For this example, another mineral source containing calcium element, that is to say $Ca(OH)_2$, was used to synthesise the calcium diglyceroxide crystals.

The general procedure mentioned above was applied using the following parameters:

A starting suspension containing 1072 g of raw materials ($Ca(OH)_2$+glycerol) with a molar ratio of (glycerol):($Ca(OH)_2$) equal to 5, per 1 kg of anhydrous solvent of glycerol (methanol);

A flow rate of 45 L/h;

500 μm milling beads predominantly made up of $ZrO_2$ (Zirmil® Y Ceramic Beads);

And carrying out a single passage in the mill.

Figure 9:
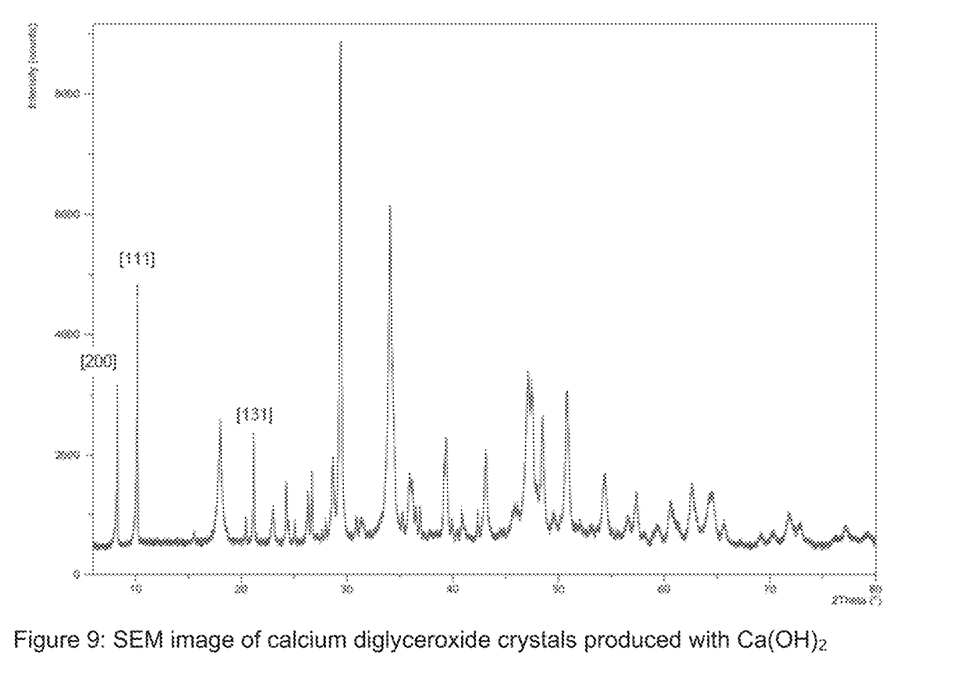
FIG. 9 is an X-ray diffractometry (XRD) spectrum of calcium diglyceroxide crystals obtained according to the method according to the invention using the following parameters: starting suspension comprising 1072 g of raw materials (glycerol+Ca(OH)$_2$) with a molar ratio of (glycerol):(Ca(OH)$_2$) equal to 5, in 1 kg of anhydrous solvent of glycerol (herein, methanol); a flow rate of the starting suspension in the mill of 45 L/h and a bead diameter of 500 µm.

With reference to FIG. 9, it is observed that the lines of the four XRD spectra, scanned successively, are fully conforming with respect to those of the reference spectrum of calcium diglyceroxide, known to those skilled in the art (CDDC deposition ref #828033), both for the angular positions thereof and for the relative intensities thereof, that is to say:

The presence of the three primary peaks is observed (crystallographic planes [200], [111] and [131]), at respectively 8.281°/10.177° and 21.179°, All the other significant peaks are present at the envisaged angles, such as 20.436°/24.466°/25.071°/26.671°/27.973°/34.446°/36.505°/36.894°/39.130°/40.850;

with substantially the envisaged intensities,

These XRD spectra also show the residual presence of unconverted matter. Indeed:

the primary peaks of Ca(OH)2 (as per JCPDS 044-1481), which are at 18.008°/28.672°/34.102° are present;

and the primary peak of CaCO3 (as per JCPDS 005-0586) which is at 29.4° is also observed Thus, it was demonstrated that calcium diglyceroxide crystals may be synthesised using $Ca(OH)_2$ by way of calcium element source raw material. Particularly, under the conditions of the general procedure mentioned, that is to say with a single passage in the mill for a flow rate of 45 L/h, it was observed that the calcium diglyceroxide crystals obtained with $Ca(OH)_2$ are slightly less pure than those obtained under similar conditions with CaO (example C). However, a conversion approaching 100% for $Ca(OH)_2$ can be envisaged, particularly by increasing the holding time in the mill.

G° Conclusion

Thus, it was demonstrated that for all the tests, a powder insoluble in the anhydrous solvent of glycerol is obtained. After testing by XRD analysis, it emerged that this powder corresponded to calcium diglyceroxide crystals (all the XRD spectra produced by the applicant show a conversion of the starting compounds into calcium diglyceroxide, the spectra indeed indicate the lines corresponding to calcium diglyceroxide, with merely a few residual traces of initial compounds).

The DTA/TGA curves were found to be fully in line with the elements of the prior art well-known to those skilled in the art, with particularly a total loss of mass after 850° C. of 75%, that may correspond to the breakdown of calcium diglyceroxide into calcium oxide (74.8%).

The images obtained by scanning electron microscopy show calcium diglyceroxide crystals. It is likewise found that the powder obtained essentially consists of well-formed crystals, the grain size distribution Dx(50) whereof is generally less than 10 μm.

Obviously according to the milling parameters, for example by adjusting the microbead sizes, it is possible to obtain crystals that are larger in size, (Dx50) up to 50 μm) or smaller ($D_x(50) < 1$ μm).

Furthermore, the laboratory mill makes it possible to produce 54 kg/h of calcium diglyceroxide. This figure could be multiplied by 10 with the addition of an acceleration accessory. Likewise, there exist industrial versions of the mill using for example up to 100 kg of beads. With this type of mill, it would consequently be possible to manufacture several tonnes of calcium diglyceroxide per hour.

The invention claimed is:

1. A method for manufacturing calcium diglyceroxide crystals that comprises at least the following steps:
   (1) placing at least one calcium element source compound in suspension in glycerol or in a homogeneous mixture of glycerol ($C_3H_8O_3$) and an anhydrous solvent of glycerol, referred to as the "starting suspension", the molar ratio of (glycerol):(calcium element source compound(s)) being greater than or equal to 2, wherein the calcium element source compound is calcium oxide (CaO), $Ca(OH)_2$, calcium acetate, calcium methanolate, or any of the combinations thereof;
   (2) milling said starting suspension at an ambient temperature of less than or equal to 50° C., in a three-dimensional liquid-phase microbead mill for a holding time of less than or equal to 15 min;
   (3) recovering, at an outlet of the mill, a suspension of calcium diglyceroxide crystals, and
   (4) optionally, washing the obtained suspension with a glycerol solvent in order to eliminate any excess glycerol,
   (5) optionally, said suspension of calcium diglyceroxide crystals is dried so as to obtain a powder of calcium diglyceroxide crystals.

2. The method according to claim 1, wherein the molar ratio of (glycerol):(calcium element source compound(s)) ranges from 2 to 10.

3. The method according to claim 2, wherein the molar ratio of (glycerol):(calcium element source compound(s)) ranges from 2 to 5.

4. The method according to claim 1, wherein the starting suspension has a holding time in the three-dimensional liquid-phase microbead mill less than or equal to 1 minute.

5. The method according to claim 4, wherein the starting suspension has a holding time in the three-dimensional liquid-phase microbead mill ranging from 5 to 25 seconds.

6. The method according to claim 5, wherein the starting suspension has a holding time in the three-dimensional liquid-phase microbead mill ranging from 10 to 20 seconds.

7. The method according to claim 1, wherein the molar ratio of (anhydrous solvent of glycerol):(glycerol) ranges from 0 to 30.

8. The method according to claim 1, wherein the molar ratio of (anhydrous solvent of glycerol):(glycerol) ranges from 2 to 15.

9. The method according to claim 1, wherein glycerol and the calcium element source compound(s) are mixed in stoichiometric proportions.

10. The method according to claim 1, wherein the anhydrous solvent of glycerol is methanol ($CH_3OH$), isopropanol or ethanol.

11. The method according to claim 1, wherein the microbeads are of spherical shape and have a mean diameter ranging from 0.05 mm to 4 mm.

12. The method according to claim 1, wherein the microbeads have a Vickers hardness measured as per the EN ISO 6507-1 standard greater than or equal to 900 HV1.

13. The method according to claim 1, wherein the microbeads have a true density ranging from 2 to 15 g/cm$^3$.

14. The method according to claim 1, wherein the milling is carried out at an ambient temperature ranging from 15° C. to 45° C.

15. The method according to claim 1, wherein the three-dimensional microbead mill comprises at least:
- a stationary milling chamber of general cylindrical shape extending along a longitudinal axis XX, said chamber being filled at least, in part, with said microbeads and comprises: at a first end at least one inlet serving to introduce said starting suspension, and at a second end, an outlet including a separating means suitable for only discharging the calcium diglyceroxide suspension formed in said chamber; and
- an agitator, arranged in the stationary milling chamber, presented in the form of an elongated rod along the longitudinal axis XX, said agitator being suitable for setting in motion the microbead/starting suspension assembly.

16. The method according to claim 15, wherein the microbeads represent, in volume, with respect to the total volume of the stationary chamber from 50% to 85%.

17. The method according to claim 15, wherein the microbeads represent, in volume, with respect to the total volume of the stationary chamber from 55% to 70%.

18. The method according to claim 1, wherein the mill operates in continuous mode.

19. The method according to claim 15, wherein the rotational speed of the agitator is greater than or equal to 100 revolutions per minute.

20. The method according to claim 1, wherein the microbeads are chosen from the group consisting of ceramic microbeads, steel microbeads, tungsten carbide microbeads, glass microbeads and any of the combinations thereof.

* * * * *